United States Patent
Baik (10) Patent No.: US 11,504,532 B2
(45) Date of Patent: Nov. 22, 2022

(54) THOREASE NEUROSTIMULATION CHEST TUBE

(71) Applicant: INTERNATIONAL PRIVATE BANK LLC, St. Thomas, VI (US)

(72) Inventor: Peter Ungjo Baik, Tulsa, OK (US)

(73) Assignee: COH HOLDCO INC., Duarte, CA (US)

(*) Notice: Subject to any disclaimer, the term of this patent is extended or adjusted under 35 U.S.C. 154(b) by 242 days.

(21) Appl. No.: 16/485,350

(22) PCT Filed: Feb. 16, 2018

(86) PCT No.: PCT/US2018/018519
§ 371 (c)(1),
(2) Date: Aug. 12, 2019

(87) PCT Pub. No.: WO2018/152420
PCT Pub. Date: Aug. 23, 2018

(65) Prior Publication Data
US 2019/0374772 A1 Dec. 12, 2019

Related U.S. Application Data

(60) Provisional application No. 62/459,691, filed on Feb. 16, 2017.

(51) Int. Cl.
*A61N 1/36* (2006.01)
*A61N 1/05* (2006.01)
(Continued)

(52) U.S. Cl.
CPC .......... *A61N 1/36021* (2013.01); *A61M 1/84* (2021.05); *A61N 1/0551* (2013.01);
(Continued)

(58) Field of Classification Search
CPC ............ A61N 1/36021; A61N 1/36034; A61N 1/0551; A61N 1/36017; A61M 1/84;
(Continued)

(56) References Cited

U.S. PATENT DOCUMENTS

RE30,750 E * 9/1981 Diack .................. A61N 1/3904
607/5
6,438,423 B1 8/2002 Rezai et al.
(Continued)

FOREIGN PATENT DOCUMENTS

GB 2414410 A 11/2005
WO 2016069829 A1 5/2016

OTHER PUBLICATIONS

Conor Mulrooney GB 2541039,Jul. 8, 2015 (Year: 2015).*

*Primary Examiner* — Catherine M Voorhees
*Assistant Examiner* — Roland Dinga
(74) *Attorney, Agent, or Firm* — Katten Muchin Rosenman LLP (57) ABSTRACT

A chest tube device with neurostimulation is provided, along with a method of electrically stimulating at least one of (i) one or more peripheral nerves and (ii) one or more nerve fibers of a thoracic region of a patient, to mitigate pain in patients undergoing chest tube implantation. The chest tube device includes a tubular member and an electro-analgesic region to provide neurostimulation to one or more peripheral nerves and/or nerve fibers of the thoracic region of the patient. The method includes electrically stimulating one or more peripheral nerves and/or nerve fibers of the thoracic region of the patient, and hyperpolarizing the one or more peripheral nerves and/or nerve fibers of the thoracic region to (i) reduce an amount of pain signals from being transmitted to the brain of the patient and/or (ii) prevent pain signals from being transmitted to the brain of the patient.

20 Claims, 3 Drawing Sheets

(51) Int. Cl.
    *A61M 1/00*     (2006.01)
    *A61M 19/00*    (2006.01)
    *A61M 25/00*    (2006.01)
    *A61M 27/00*    (2006.01)

(52) U.S. Cl.
    CPC ..... *A61N 1/36017* (2013.01); *A61N 1/36034* (2017.08); *A61M 19/00* (2013.01); *A61M 25/0068* (2013.01); *A61M 27/00* (2013.01); *A61M 2205/054* (2013.01); *A61M 2210/101* (2013.01)

(58) Field of Classification Search
    CPC .. A61M 19/00; A61M 25/0068; A61M 27/00; A61M 2205/054; A61M 2210/101
    See application file for complete search history.

(56) References Cited

U.S. PATENT DOCUMENTS

| | | | |
|---|---|---|---|
| 6,861,570 B1 | 3/2005 | Flick | |
| 8,433,423 B2* | 4/2013 | Demarais | A61N 1/36117 607/118 |
| 2010/0268156 A1 | 10/2010 | Milacek et al. | |
| 2011/0237920 A1 | 9/2011 | Glaser et al. | |
| 2017/0333714 A1* | 11/2017 | Ahmad | A61N 1/0504 |

\* cited by examiner

THOREASE NEUROSTIMULATION CHEST TUBE

CROSS-REFERENCE TO RELATED APPLICATION

This application claims the benefit of U.S. Provisional Application No. 62/459,691 entitled "THOREASE NEUROSTIMULATION CHEST TUBE," filed Feb. 16, 2017, the entirety of which is incorporated herein by reference.

TECHNICAL FIELD

The present disclosure generally relates to a chest tube device with neurostimulation to both (i) drain air and/or fluid (e.g., pleural effusion and/or blood) from the thoracic region and (ii) electrically stimulate the peripheral nerves and/or nerve fibers of the thoracic region to reduce and/or prevent the propagation of pain signals that generally result from the placement of a chest tube in the thoracic region.

BACKGROUND OF THE DISCLOSURE

During various surgical procedures to the thoracic region, for example, lung resection or due to trauma to this region, including, for example, gunshots, broken ribs, or car accidents, chest tubes are often placed in the thoracic region to monitor bleeding or air leakage, and to drain any excess pleural fluid. Chest tubes are also placed in the thoracic region due to various medical conditions, such as cancer, pleural effusion, pneumothorax, hemothorax, chylothorax, etc. In fact, it is estimated that over 900,000 chest tubes are medically used, per year, in the United States. However, patients often experience pain because of the placement of the chest tube. In particular, the chest tube is usually placed just above one or more of the ribs to avoid damage to the intercostal nerve, artery, and vein. However, for proper placement, it may be necessary to place the chest tube at an extreme angle to reach the apex of the lung. This extreme angle can result in pressure to the nerve(s) just above the chest tube, including, for example, the intercostal nerves. Also, as the chest tube touches the parietal pleura, pain receptors are activated. In addition, as the patient breathes, adjacent ribs are torqued, causing the patient more discomfort. This discomfort can be severe and prevent the patient from breathing properly, which, in turn, can cause atelectasis (e.g., collapse of the airspace in the lung) and/or subsequent pneumonia (e.g., infection of the lung). Moreover, in order to recover from thoracic procedures, patients need to properly breathe to heal the wounded area and/or remove excess pleural fluid and/or air from the area surrounding the lungs.

To optimize recovery from thoracic procedures, when chest tubes are used with a patient, current medical practice uses various types of pain management to decrease or eliminate the pain associated with the placement of the chest tube. For optimal pain management, a multimodal therapy is generally used. Multimodal therapy includes, for example, IV pump infusions (e.g., morphine, hydromorphone, ketamine, etc.), oral opioids, non-steroid anti-inflammatory drugs (NSAID), intercostal/paravertebral nerve block, systemic non-opioid postsurgical analgesics, local or intrapleural analgesia, and epidurals. In addition, patient-controlled analgesia (PCA) administered narcotics are often used to alleviate pain while a chest tube is present. The use of opioids in general and PCA narcotics in particular, can decrease lung ventilation and increase constipation, urinary retention, and the need to transition to oral pain medications, prior to the patient being sent home. Oral pain medications, however, are associated with various side effects that are not ideal. While low ventilation increases the risk for pneumonia, the large combined dose of narcotics exacerbates the possibility of opioid dependence, addiction and hyperalgesic syndrome, with a negative impact on the immunologic response. In addition to potential side effects, the administration of opioids may induce drug tolerance, in which case, the drugs are no longer effective.

Devices that incorporate electrical stimulation or neurostimulation have also been used to attempt to address various pain conditions, including, for example, chronic pain that occurs after a chest tube is removed (e.g., post-thoracotomy pain syndrome (PTPS)), which occurs in up to 50% of patients.

Such devices include transcutaneous electrical nerve stimulation (TENS), spinal cord stimulation (SCS), and peripheral nerve stimulation (PNS) devices. TENS is a non-invasive method in which electrodes are attached to a patient's skin, and electrical stimulation is thereafter applied. In contrast, SCS and PNS involve more invasive procedures. In SCS, electrical stimulation is applied to the nerves in the spine via an implanted device and/or electrode(s), thus preventing a pain signal from being transmitted to the brain. There are generally two types of SCS systems. The first type of SCS system is transcutaneous, in which an external radio frequency transmitter is used to transmit the electrical stimulation to the implanted device and/or electrode(s).

The second type of SCS system is fully implantable, which does not require any external transmitter. In PNS, electrical stimulation is applied to the peripheral nerve(s) responsible for the pain via an implanted device and/or electrode(s).

For example, the electrical stimulation can be applied directly to the involved peripheral nerves, or in close proximity to the area(s) of maximal pain (e.g., peripheral nerve field stimulation (PNFS)). As discussed above, however, TENS, SCS, and PNS devices are also used to treat chronic pain that occurs after the chest tube is removed.

Accordingly, there is a need to provide a device that would function as a chest tube (i.e., by draining air and/or fluid (e.g., pleural effusion and/or blood) from the thoracic region), while reducing, suppressing, and/or eliminating the pain associated with the chest tube being placed in the thoracic region of a patient, when the chest tube is within the patient. Such a device could potentially reduce and/or eliminate the use of painkillers (e.g., NSAIDs and/or opioids), epidural anesthesia, intercostal/paravertebral nerve blocks, intravenous patient-controlled analgesia (PCA) administered narcotics, and/or IV pump infusions with local anesthetics. Moreover, such a device could potentially reduce and/or eliminate the use of various types of pain management, including, for example, neurostimulation devices, that are used to treat chronic pain that occurs after a chest tube is removed, by preventing the chronic pain from occurring altogether.

The description provided in the background section should not be assumed to be prior art merely because it is mentioned in or associated with the background section. The background section may include information that describes one or more aspects of the subject technology.

BRIEF SUMMARY OF THE DISCLOSURE

At least some embodiments of the present disclosure provide a chest tube device with neurostimulation to both (i)

drain air and/or fluid (e.g., pleural effusion and/or blood) from the thoracic region and (ii) electrically stimulate one or more peripheral nerves and/or nerve fibers of the thoracic region to reduce and/or prevent the propagation of pain signals that generally result from the placement of a chest tube in the thoracic region of a patient.

At least some embodiments of the present disclosure provide such a chest tube device with neurostimulation that will address both pleural drainage and pain management issues within a single procedure.

According to one aspect, a chest tube device with neurostimulation is provided. The chest tube device includes a tubular member and an electro-analgesic region to provide neurostimulation to at least one of (i) one or more peripheral nerves and (ii) one or more nerve fibers of the thoracic region of the patient. In one embodiment, the tubular member of the chest tube device includes a plurality of drainage holes to drain at least one of (i) blood, (ii) pleural effusion and (iii) air from the thoracic region. In another embodiment, the electro-analgesic region comprises at least one of (i) a conductive wire mesh, (ii) a stimulation sleeve, (iii) a conductive material, (iv) a conductive polymer, (v) electrostimulating leads, and (vi) one or more electrodes. In another embodiment, the chest tube device further includes a pulse generator to provide electrical signals to the electro-analgesic region. In yet another embodiment, the chest tube device includes a controller to adjust at least one of (i) a voltage, (ii) a current, (iii) a frequency, (iv) a duration, and (v) a waveform of electrical signals provided to the electro-analgesic region.

According to another aspect, a chest tube device with neurostimulation is provided. The chest tube device includes (a) a tubular member, (b) an electro-analgesic region to provide neurostimulation to at least one of (i) one or more peripheral nerves and (ii) one or more nerve fibers of a thoracic region of a patient, (c) a suction device to assist in draining at least one of blood, pleural effusion, and air from the thoracic region, and (d) a pulse generator that provides electrical signals to the electro-analgesic region.

According to another aspect, a method is provided of reducing pain associated with the placement of a chest tube in a thoracic region of a patient. The method includes inserting a chest tube device into a pleural space of a patient, between the lung and chest wall and at least one of the ribs of the patient, and electrically stimulating at least one of (i) one or more peripheral nerves and (ii) one or more nerve fibers of the thoracic region of the patient. In one embodiment, the step of electrically stimulating the at least one of (i) one or more peripheral nerves and (ii) one or more nerve fibers of the thoracic region hyperpolarizes the at least one of (i) one or more peripheral nerves and (ii) one or more nerve fibers of the thoracic region to reduce an amount of pain signals from being transmitted to the brain of the patient. In another embodiment, the step of electrically stimulating the at least one of (i) one or more peripheral nerves and (ii) one or more nerve fibers of the thoracic region is provided by an electro-analgesic region that is exposed on a surface of the chest tube device. According to yet another aspect, a method is provided of suppressing pain associated with the placement of a chest tube in a thoracic region of a patient. The method includes inserting a chest tube device into a pleural space of a patient, between the lung and chest wall and at least one of the ribs of the patient, and electrically stimulating at least one of (i) one or more peripheral nerves and (ii) one or more nerve fibers of the thoracic region of the patient. In one embodiment, the step of electrically stimulating the at least one of (i) one or more peripheral nerves and (ii) one or more nerve fibers of the thoracic region hyperpolarizes the at least one of (i) one or more peripheral nerves and (ii) one or more nerve fibers of the thoracic region to prevent pain signals from being transmitted to the brain of the patient. In yet another embodiment, the step of electrically stimulating the at least one of (i) one or more peripheral nerves and one or more nerve fibers of the thoracic region is provided by an electro-analgesic region that is exposed on a surface of the chest tube device.

According to yet another aspect, a method of mitigating pain associated with the placement of a chest tube in a thoracic region of a patient by at least one of (i) reducing an amount of pain signals from being transmitted to the brain of the patient and (ii) preventing pain signals from being transmitted to the brain of the patient is provided. The method includes (a) inserting a chest tube device into a pleural space of a patient, between the lung and chest wall and at least one of the ribs of the patient, and (b) electrically stimulating at least one of (i) one or more peripheral nerves and (ii) one or more nerve fibers of the thoracic region of the patient.

According to another aspect, a method of electrically stimulating at least one of (i) one or more peripheral nerves and (ii) one or more nerve fibers of a thoracic region of a patient, to reduce pain in patients undergoing chest tube implantation is provided. The method includes electrically stimulating at least one of (i) one or more peripheral nerves and (ii) one or more nerve fibers of the thoracic region of the patient, and hyperpolarizing the at least one of (i) one or more peripheral nerves and (ii) one or more nerve fibers of the thoracic region to reduce an amount of pain signals from being transmitted to the brain of the patient.

According to a further aspect, a method of electrically stimulating at least one of (i) one or more peripheral nerves and (ii) one or more nerve fibers of a thoracic region of a patient, to suppress pain in patients undergoing chest tube implantation is provided. The method includes electrically stimulating at least one of (i) one or more peripheral nerves and (ii) one or more nerve fibers of the thoracic region of the patient, and hyperpolarizing at least one of (i) one or more peripheral nerves and (ii) one or more nerve fibers of the thoracic region to prevent pain signals from being transmitted to the brain of the patient. According to yet another aspect, a method of electrically stimulating at least one of (i) one or more peripheral nerves and (ii) one or more nerve fibers of a thoracic region of a patient, to mitigate pain in patients undergoing chest tube implantation is provided. The method includes electrically stimulating at least one of (i) one or more peripheral nerves and (ii) one or more nerve fibers of the thoracic region of the patient, and hyperpolarizing at least one of (i) one or more peripheral nerves and (ii) one or more nerve fibers of the thoracic region to at least one of (i) reduce an amount of pain signals from being transmitted to the brain of the patient and (ii) prevent pain signals from being transmitted to the brain of the patient.

The description in this summary section may provide some illustrative examples of the disclosure. This section is not intended to be a broad overview or to identify essential elements of the disclosure.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

The present disclosure generally relates to a chest tube device with neurostimulation to both (i) drain air and/or fluid (e.g., pleural effusion and/or blood) from the thoracic region and (ii) electrically stimulate the peripheral nerves and/or nerve fibers of the thoracic region to reduce and/or prevent the propagation of pain signals that typically result from the placement of a chest tube in the thoracic region of a patient. More specifically, the present disclosure relates to a chest tube device that incorporates neurostimulation to address both pleural drainage and pain management issues within a single procedure.

In one embodiment, the chest tube device comprises (i) a tubular member with drainage holes to drain pleural effusion, blood, and/or air from an area surrounding the lungs of a patient, and (ii) an electro-analgesic region to provide neurostimulation and/or electrical stimulation to peripheral nerves and/or nerve fibers of the thoracic region. The neurostimulation and/or electrical stimulation of the peripheral nerves and/or nerve fibers of the thoracic region can be provided by, for example, a wire mesh, a stimulation sleeve, conductive materials, conductive polymers, electro-stimulating leads, and/or electrodes provided to a surface of the chest tube device. Because different nerves and nerve fibers (e.g., A-beta, A-delta, or C neurons) require different types of neurostimulation, in one embodiment, the chest tube device is capable of electrically stimulating all three tissue levels simultaneously (i.e., the cutaneous, subcutaneous, and musculoskeletal tissues), to more effectively alleviate the pain associated with the placement of a chest tube in the thoracic region of a patient.

Figure 1:
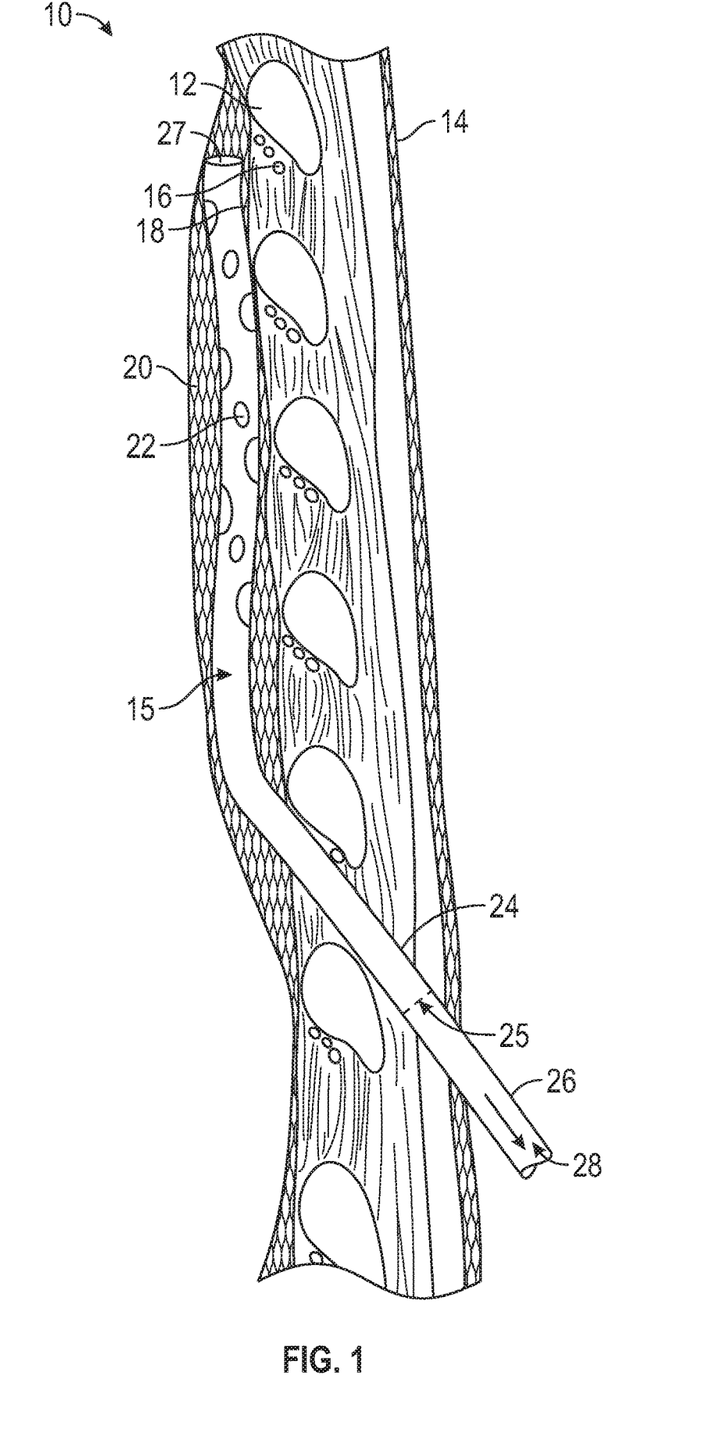
FIG. 1 illustrates a diagram of a chest tube device according to an embodiment of the present disclosure.

Turning now to the drawings, FIG. 1 illustrates a diagram of a chest tube device 15 that is placed within the thoracic region of a patient, according to an embodiment of the present disclosure. In the embodiment of FIG. 1, the chest tube device 15 is placed within the skin 14 of the patient and into the pleural space or cavity 20 between the lung 10 and chest wall and at least one of the ribs 12. In this embodiment, the pleural space or cavity 20 includes pleural effusion (e.g., fluid or blood) and/or air that needs to be drained. Accordingly, the chest tube device 15 includes a plurality of drainage holes 22 to drain blood, pleural effusion and/or air from the pleural space or cavity 20. The drained blood, pleural effusion and/or air 28 is drawn out of the chest tube device 15 and, preferably, into a reservoir and/or drainage system (not shown). In one embodiment, the chest tube device 15 is connected to a suction device, one-way valve, and/or vacuum source (e.g., PLEUR-EVAC®) to assist in the drainage of any blood, pleural effusion and/or air from the pleural space or cavity 20 (see, e.g., FIG. 2). In yet another embodiment, the chest tube device 15 is adapted to connect to various suction devices, one-way valves, and/or vacuum sources (e.g., PLEUR-EVAC®) that are currently on the market. In the embodiment of FIG. 1, the chest tube device 15 further includes an electro-analgesic region 24 on an exterior surface of the chest tube device 15 that provides neurostimulation and/or electrical stimulation to the peripheral nerves and/or nerve fibers of the thoracic region. In particular, the electro-analgesic region 24 can provide neurostimulation and/or electrical stimulation to, for example, the nerves and/or nerve fibers of the parietal pleura 18 and/or the intercostal nerves 16. As discussed in more detail below, the electro-analgesic region 24 comprises, for example, a wire mesh, a stimulation sleeve, conductive materials, conductive polymers, electro-stimulating leads, and/or electrodes provided to a surface of the chest tube device 15 to provide the neurostimulation and/or electrical stimulation. While the embodiment of FIG. 1 illustrates the electro-analgesic region 24 being disposed on the exterior surface of the chest tube device 15, the electro-analgesic region 24 could alternatively be disposed within the interior surface of the chest tube device 15. The electro-analgesic region 24 preferably extends from a point 25 on the chest tube device 15 that is positioned just within the patient's skin 14 to an end 27 of the chest tube device 15. While the embodiment of FIG. 1 illustrates the electro-analgesic region 24 comprising a continuous region that extends the entire distance from the point 25 on the chest tube device 15 to the end 27 of the chest tube device 15, the electro-analgesic region 24 could, alternatively, comprise one or more discontinuous regions that are disposed in the area between the point 25 on the chest tube device 15 and the end 27 of the device. As further shown in the embodiment of FIG. 1, the chest tube device 15 also includes a non-electro-analgesic region 26 that does not provide any neurostimulation and/or electrical stimulation. This non-electro-analgesic region 26 is provided from at least the point 25 on the chest tube device 15 that is positioned just within the patient's skin 14 to the remainder of the device 15 that extends outside of the patient's body and skin 14. In one embodiment, the chest tube device 15 is connected to an external device that includes, for example, a power source and a pulse generator to provide the electrical signals to the electro-analgesic region 24 of the chest tube device 15 and to allow for the neurostimulation and/or electrical stimulation (see, e.g., FIG. 2).

Figure 2:
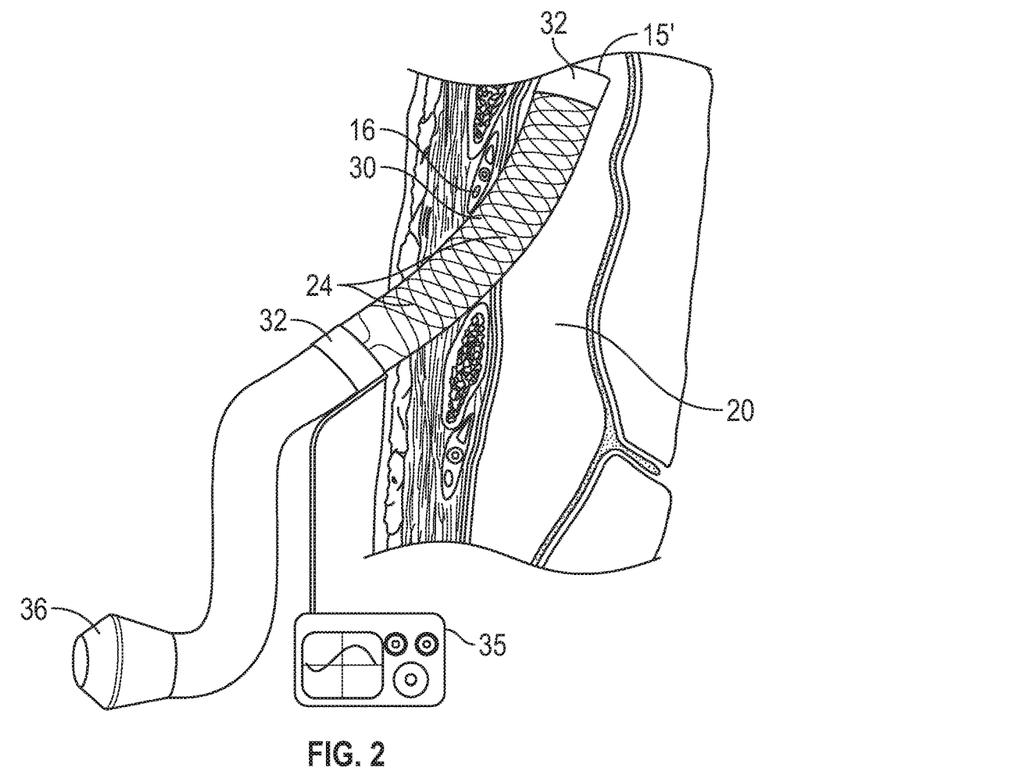
FIG. 2 illustrates a diagram of a chest tube device according to another embodiment of the present disclosure.

FIG. 2 is a diagram illustrating another embodiment of a chest tube device 15'. As shown in FIG. 2, the chest tube device 15' is positioned within the pleural space or cavity 20 that surrounds the lung and may include excess blood, pleural effusion, and/or air. In the embodiment of FIG. 2, the chest tube device 15' has an apical posterior placement, which is also the placement used for the chest tube device 15 illustrated in the embodiment of FIG. 1, to ensure the chest tube device 15' reaches the apex of the lung and to allow for effective drainage of any excess blood, pleural effusion, and/or air. As shown in the embodiment of FIG. 2, the chest tube device 15' compresses the intercostal nerve 16 at least a region 30 of the chest wall, because of respiration. The chest tube device 15' also includes the electro-analgesic region or area 24 (described above) on a surface of the chest tube device 15' that provides neurostimulation and/or electrical stimulation to the peripheral nerves and/or nerve fibers of the thoracic region. For example, in one embodiment, the electro-analgesic region or area 24 of the chest tube device 15' provides neurostimulation and/or electrical stimulation to the region 30 of the chest wall that compresses the intercostal nerve 16. As discussed in more detail below, by electrically stimulating the region 30 of the chest wall that compresses the intercostal nerve 16, as well as the other peripheral nerves and/or nerve fibers of the thoracic region, the nerves and/or nerve fibers can be hyperpolarized, which blocks the transduction of pain signals to the brain. In the embodiment of FIG. 2, the electro-analgesic region or area 24 is disposed on either the exterior or interior surface of the chest tube device 15'. In another embodiment, the electro-analgesic region 24 could, alternatively, be imbedded within the chest tube device 15'. The chest tube device 15' of FIG. 2 further includes a pair of markers 32 (e.g., distance markers) that assists a physician, nurse, or other medical technician to properly place the chest tube device 15' within the thoracic region of a patient, and to ensure the chest tube device 15' is optimally placed in relation to the patient's skin for optimal hyperpolarization of the intercostal nerve 16 (as discussed in more detail below). In the embodiment of FIG. 2, the chest tube device 15' is also connected to an external device 35 that includes, for example, a power source and a pulse generator to provide the electrical signals to the electro-analgesic region or area 24 of the chest tube device 15' and to allow for the neurostimulation and/or electrical stimulation.

The power source for the external device 35 can be an A/C adapter, battery operated and/or rechargeable. In one embodiment, the external device 35 further includes a controller to control the level of stimulation and/or the stimulation program as per each patient's physical requirements. The controller can allow for a physician, nurse, medical technician, and/or patient to select a specific stimulation program with the possibility of altering the voltage, current, frequency, and/or duration of the electrical signals to thereby promote pain relief based on the particular patient and the specifically selected program. The controller may include a remote control, and the power source for the controller can be an A/C adapter, battery operated and/or rechargeable. In the embodiment of FIG. 2, the chest tube device 15' is further connected to a suction device or pump 36. This suction pump 36 can assist in, for example, the drainage of any blood, pleural effusion and/or air from the pleural space or cavity 20 that surrounds the lung.

Figure 3:
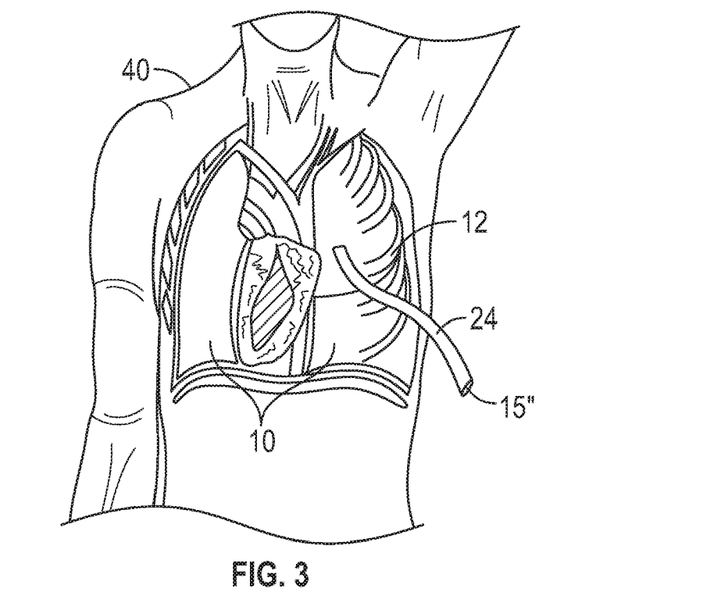
FIG. 3 is a diagram of the placement of a chest tube device in a patient according to an embodiment of the present disclosure.

FIG. 3 is a diagram of the placement of a chest tube device 15" in a patient 40 according to an embodiment of the present disclosure. As shown in FIG. 3, the chest tube device 15" is placed within the thoracic region of the patient 40. In particular, the chest tube device 15" is placed within an area between the lung 10 and/or chest wall and at least one of the ribs 12 that may include excess blood, pleural effusion, and/or air. In the embodiment of FIG. 3, the chest tube device 15" has an apical posterior placement, which, as discussed above, is also the placement used for the chest tube device 15, 15' illustrated in the embodiments of FIGS. 1 and 2, to ensure the chest tube device 15" reaches the apex of the lung 10 and to allow for effective drainage of any blood, excess pleural effusion, and/or air. In the embodiment of FIG. 3, the chest tube device 15" includes the electro-analgesic region or area 24 that is disposed on an exterior surface of the chest tube device 15". Although the embodiment of FIG. 3 illustrates the electro-analgesic region or area 24 being disposed on the exterior surface of the chest tube device 15", as discussed above, the electro-analgesic region or area 24 could alternatively be disposed on an interior surface of the chest tube device 15". In addition, in the embodiment of FIG. 3, the electro-analgesic region or area 24 extends along the chest tube device 15" from a region of the chest tube device 15" that is disposed outside of the body of the patient 40 to a region of the chest tube device 15" that is between the lung 10 and/or chest wall and at least one of the ribs 12. However, the electro-analgesic region or area 24 could alternatively be disposed (e.g., applied) on a region of the chest tube device 15" that is entirely within the body of the patient 40 when the chest tube device 15" is in position (see, e.g., FIGS. 1 and 2).

Figure 4A:
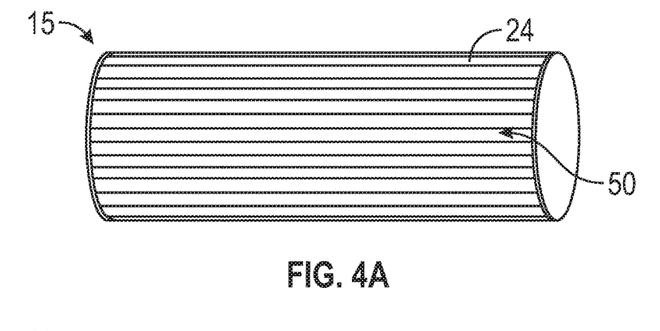
FIGS. 4A, 4B, 4C, 4D, 4E, and 4F illustrate diagrams of various structures incorporating conductive materials for the electro-conductive region of a chest tube device according to various embodiments of the present disclosure.
Figure 4B:
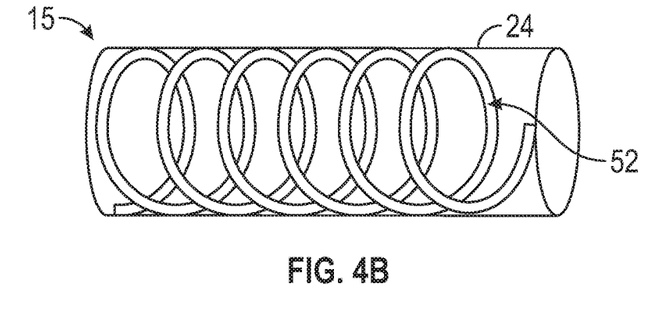
Figure 4C:
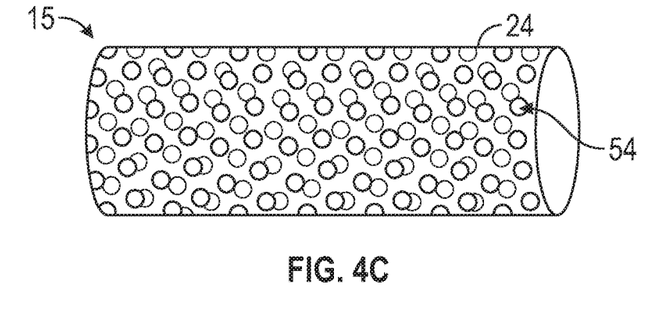

FIGS. 4A-4F illustrate various embodiments for the electro-analgesic region or area 24 of the chest tube device 15, 15', 15" illustrated in FIGS. 1-3. In the embodiment of FIG. 4A, the electro-analgesic region or area 24 comprises strips of conductive material 50 that extend horizontally along the electro-analgesic region or area 24 of the chest tube device 15 and provide the neurostimulation or electrical stimulation. The strips of conductive material 50 can be composed of, for example, a metal (e.g., gold and/or silver), polymer (e.g., polyaniline, polypyrrole, polythiophene and/or derivatives of polythiophene, such as poly(3,4-ethylenedioxythiophene) (PEDOT)), carbon-based materials (e.g., graphene and/or ribbons of carbon nanotubes), or any other clinically-acceptable electrically conductive material, composites, and/or combinations of the foregoing. While the embodiment of FIG. 4A illustrates the strips of conductive material 50 extending horizontally along the chest tube device 15, the strips of conductive material 50 could alternatively extend vertically, diagonally, or any combination of horizontally, vertically, and/or diagonally, along the device 15. In the embodiment of FIG. 4B, the electro-analgesic region or area 24 comprises a coil(s) of conductive material 52 that extends along the electro-analgesic region or area 24 of the chest tube device 15 and provides the neurostimulation or electrical stimulation. The coil of conductive material 52 is, preferably, helically wound around the chest tube device 15 and is composed of, for example, a metal (e.g., gold and/or silver), polymer (e.g., polyaniline, polypyrrole, polythiophene and/or derivatives of polythiophene, such as poly(3,4-ethylenedioxythiophene) (PEDOT)), carbon-based materials (e.g., graphene and/or ribbons of carbon nanotubes), or any other clinically-acceptable electrically conductive material, composites, and/or combinations of the foregoing. The coil of conductive material 52 of FIG. 4B could also comprise a plurality of coils and/or a conductive wire mesh to provide the neurostimulation or electrical stimulation to the electro-analgesic region or area In the embodiment of FIG. 4C, the electro-analgesic region or area 24 comprises a plurality of particles of conductive material 54 that extends along the electro-analgesic region or area 24 of the chest tube device 15 and provides the neurostimulation or electrical stimulation. The plurality of particles or network of particles of conductive material 54 can be composed of, for example, a metal (e.g., gold and/or silver), polymer (e.g., polyaniline, polypyrrole, polythiophene and/or derivatives of polythiophene, such as poly(3,4-ethylenedioxythiophene) (PEDOT)), carbon-based materials (e.g., graphene and/or ribbons of carbon nanotubes), or any other clinically-acceptable electrically conductive material, composites, and/or combinations of the foregoing. The particles of conductive material 54 of FIG.

Figure 4D:
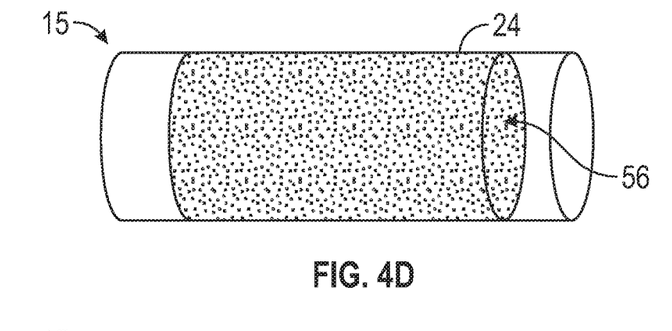
Figure 4E:
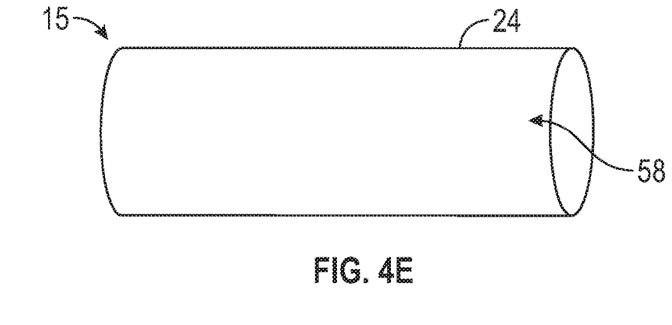
Figure 4F:
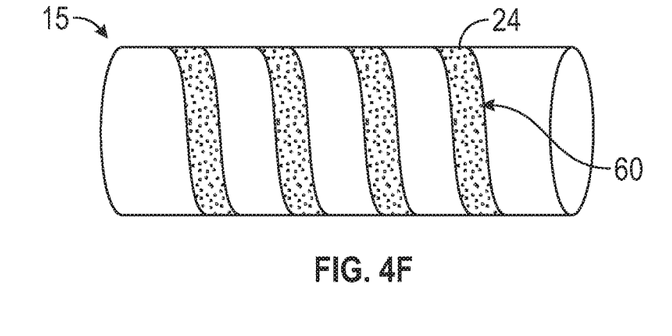

4C can be of the same size or different sizes along the electro-analgesic region or area 24 of the chest tube device 15. Moreover, the particles of conductive material 54 of FIG. 4C, preferably, have an optimal percolation threshold to conduct the required electrical signal for the neurostimulation or electrical stimulation. In the embodiment of FIG. 4D, the electro-analgesic region or area 24 comprises a sheath or sleeve of conductive material 56 that extends along the electro-analgesic region or area 24 of the chest tube device 15 and provides the neurostimulation or electrical stimulation. The sheath or sleeve of conductive material 56 can be composed of, for example, a metal (e.g., gold and/or silver), polymer (e.g., polyaniline, polypyrrole, polythiophene and/or derivatives of polythiophene, such as poly(3,4-ethylenedioxythiophene) (PEDOT)), carbon-based materials (e.g., graphene and/or ribbons of carbon nanotubes), or any other clinically-acceptable electrically conductive material, composites, and/or combinations of the foregoing. The sheath or sleeve of conductive material 56 of FIG. 4D can be a variety of shapes, sizes, lengths and/or thicknesses to provide the most effective neurostimulation or electrical stimulation to the electro-analgesic region or area 24 of the chest tube device 15. By providing a sheath or sleeve of conductive material 56, the sheath or sleeve can be easily placed onto a pre-manufactured chest tube device 15 or adapted to fit onto existing chest tubes, prior to placement of the chest tube device 15 into the thoracic region of the patient. In the embodiment of FIG. 4E, the electro-analgesic region or area 24 comprises an electrically conductive polymer 58 that is coated onto the electro-analgesic region or area 24 of the chest tube device 15. The electrically conductive polymer 58 can be composed of, for example, hydrogels, including those used on, for example, ECG or EEG leads, that are composed of, for example, cross-linked polymers (e.g., polyethylene oxide, polyAMPS, and polyvinylpyrrolidone), polyaniline, polypyrrole, polythiophene and/or derivatives of polythiophene, such as Poly(3,4-ethylenedioxythiophene) (PEDOT), or any other electrically conductive material. The electrically conductive polymer 58 is coated onto either or both of the exterior and/or interior surface of the chest tube device 15 to provide the neurostimulation or electrical stimulation to the electro-analgesic region or area 24 of the chest tube device 15. The electrically conductive polymer 58 could also comprise a composite of polymers. In one embodiment, the neurostimulation or electrical stimulation is provided to the electro-analgesic region or area 24 of the chest tube device 15 by electrodes and/or electro-stimulating leads provided along the exterior and/or interior surface of the chest tube device 15. In the embodiment of FIG. 4F, ring-shaped electrodes or electrically conductive rings 60 are provided along the exterior surface of the chest tube device 15 to provide the neurostimulation or electrical stimulation to the electro-analgesic region or area 24 of the chest tube device 15. The electrodes or rings 60 of FIG. 4F can be glued or otherwise affixed to the exterior surface of the electro-analgesic region or area 24 of the chest tube device 15. Alternatively or additionally, the electrodes or rings 60 of FIG. 4F could be wedged into place onto the electro-analgesic region or area 24 of the chest tube device 15 to provide a smoother profile, if necessary. Alternatively, in one embodiment, the electrodes or rings 60 of FIG. 4F could be imbedded within the interior of the chest tube device 15 to provide the electro-analgesic region or area 24. The electrodes or rings 60 of FIG. 4F can be positive electrodes, negative electrodes, or both. In one embodiment, two to five electrodes or rings are provided to the exterior surface of the electro-analgesic region or area 24 of the chest tube device 15, such that a selected set of the electrodes can be manually set to transmit certain electrical signals for a selected stimulation therapy. While the embodiments of FIGS. 4A-4F illustrate various embodiments for the electro-analgesic region or area 24 of the chest tube device 15, one or a combination of the illustrated embodiments can be provided to the electro-analgesic region or area 24 to provide the neurostimulation or electrical stimulation to the electro-analgesic region or area 24 of the chest tube device 15. Although not shown in FIGS. 4A-4F, the outer surface of the chest tube device 15, including the electro-analgesic region or area 24 of the chest tube device 15, can include ridges, grooves, and/or spikes (e.g., micro- and/or nano-features) to ensure optimal delivery of electrical signals to the electro-analgesic region or area 24 and/or the peripheral nerves and/or nerve fibers of the thoracic region (as discussed below) without adversely affecting insertion and/or removal of the chest tube device 15. In one embodiment, the ridges, grooves, and/or spikes (e.g., micro- and/or nano-features) provided along the outer surface of the chest tube device 15 are biodegradable, which allows for, for example, (i) these features to aid with the removal of the chest tube device 15 from the body and/or (ii) these features to be easily absorbed by the body, in the event that these features break off from the chest tube device 15.

In each of the embodiments for the electro-analgesic region or area 24 of the chest tube device 15 discussed above (i.e., FIGS. 4A-4F), the conductive material(s), conductive polymer(s), and/or electrodes are connected to, for example, a power source and a pulse generator to provide electrical signals to the conductive material(s), conductive polymer(s), and/or electrodes of the electro-analgesic region or area 24 (see, e.g., the external device 35 of FIG. 2). For example, in one embodiment, the conductive material(s), conductive polymer(s), and/or electrodes are connected to a power source and a pulse generator by electrical leads to transfer the electrical signals to the conductive material(s), conductive polymer(s), and/or electrodes of the electro-analgesic region or area 24. Once the electrical signals are transferred to the conductive material(s), conductive polymer(s), and/or electrodes of the electro-analgesic region or area 24, the electrical signals, in the form of neurostimulation or electrical stimulation, can be transferred to the peripheral nerves and/or nerve fibers of the thoracic region, including, for example, the intercostal nerve(s) and/or the parietal pleura. The neurostimulation or electrical stimulation is transferred to the peripheral nerves and/or nerve fibers of the thoracic region due to the close proximity of the electro-analgesic region or area 24 of the chest tube device 15 to these peripheral nerves and/or nerve fibers, once the chest tube device 15 is placed within the thoracic region of the patient (see, e.g., FIGS. 1-3). The electro-analgesic region or area 24 of the chest tube device 15 would likely not be in direct contact with these peripheral nerves and/or nerve fibers. Thus, the neurostimulation or electrical stimulation would be transferred to the peripheral nerves and/or nerve fibers of the thoracic region similar to that seen with TENS technology. By electrically stimulating the nerves and/or nerve fibers of the thoracic region, the nerves and/or nerve fibers can be hyperpolarized, which interferes with, prevents, and/or reduces the propagation of pain signals to the brain. The electrical stimulation of the nerves and/or nerve fibers of the thoracic region can decrease the pain associated with the placement of the chest tube by, for example, stimulating the afferent pain fibers (e.g., the $A\alpha$, $A\beta$, $A\delta$, and C fibers) to prevent and/or reduce the propagation of pain signals.

Moreover, since both the intercostal nerve and the other peripheral nerves and/or nerve fibers in the pleural tissue are generally involved in conducting pain when a chest tube is placed, by electrically stimulating the electro-analgesic region or area 24 of the chest tube device 15, preferably, along the entire length of the electro-analgesic region or area 24, both the intercostal nerve and the other peripheral nerves and/or nerve fibers of the thoracic region can be hyperpolarized to prevent and/or reduce the pain signals from being sent to the brain. Accordingly, the patient should have reduced, suppressed, and/or no pain once the chest tube is placed in the thoracic region, due to the electrical stimulation and/or hyperpolarization of the intercostal nerve and the other peripheral nerves and/or nerve fibers of the thoracic region. Moreover, since the electro-analgesic region or area 24 of the chest tube device 15 penetrates the skin and tissues of the patient (see, e.g., FIGS. 1-3), the electrical stimulation of the electro-analgesic region or area 24 would be capable of electrically stimulating all three tissue levels simultaneously (i.e., the cutaneous, subcutaneous, and musculoskeletal tissues), along with the intercostal nerve and the other peripheral nerves and/or nerve fibers of the thoracic region, to more effectively alleviate the pain associated with the placement of a chest tube in the thoracic region of a patient. In addition, as discussed above, the outer surface of the chest tube device 15, including the electro-analgesic region or area 24 of the chest tube device 15, can include, for example, ridges, grooves, and/or spikes (e.g., micro- and/or nano-features) to ensure optimal delivery of the electrical signals to the electro-analgesic region or area 24 and/or the peripheral nerves and/or nerve fibers of the thoracic region. However, the inclusion of the ridges, grooves, and/or spikes (e.g., micro- and/or nano-features) to the outer surface of the chest tube device 15 does not affect the insertion and/or removal of the chest tube device 15 from the body.

As discussed above, the electro-analgesic region or area 24 of the chest tube device 15 that includes, for example, the conductive material(s), conductive polymer(s), and/or electrodes of FIGS. 4A-4F, is connected to, for example, a pulse generator to provide the electrical signals to the electro-analgesic region or area 24 (see, e.g., the external device 35 of FIG. 2). The electrical signals travel from the pulse generator to the electro-analgesic region or area 24 of the chest tube device 15 by, for example, transmitting the signals through the skin using technology similar to TENS or transmitting the signals using leads connected between the pulse generator and the electro-analgesic region or area 24 using technology similar to PNFS and/or SCS. The pulse generator preferably includes a controller to modulate the parameters of the electrical signals and/or electrical stimulation. For example, the voltage, current, frequency, and/or duration of the electrical signals can be selected to promote pain relief by interfering with the peripheral nerves and/or nerve fibers that carry pain impulses to the spinal cord and/or brain. Moreover, the voltage, current, frequency, and/or duration of the electrical signals can be varied to offer each patient individualized therapy to optimally reduce their pain.

Examples of electrical signals used to promote pain relief are shown in Table 1 below:

TABLE 1

| Method of Transmitting Electrical Signals | Voltage | Current | Frequency | Duration |
|---|---|---|---|---|
| Exemplary TENS parameters with signals transferred through the skin | | 0-700 mA<br>0-20 mA<br>12 mA | 1-150 Hz<br>0-120 Hz<br>3 Hz | 50-300 µs<br>100 µs-100 ms<br>100 ms<br>2-200 ms |
| Exemplary PNS/PNFS parameters for peripheral nerve and/or peripheral nerve field stimulation | 2-4.8 V<br>0-14 V | 2 mA<br>3 mA<br>2.4 mA<br>Up to 12 mA | 2 Hz (motor)<br>50 Hz (sensory)<br>40-240 Hz<br>7-200 Hz<br>15, 25, 30, 40 Hz<br>Up to 1000 Hz | 140-400 µs<br>50-400 µs<br>740-790 ms<br>140 ms<br>150 ms<br>Up to 1000 µs |
| Exemplary SCS parameters for spinal cord stimulation | 2-7 V<br>4.6 V | 0-25.4 mA | 0.5-1200 Hz<br>4-80 Hz<br>10 kHz | 10-2000 µs<br>40-1000 µs |

In view of the foregoing, the electrical signals provided from the pulse generator to the electro-analgesic region or area 24 can be programmed with a variety of parameters for voltage, current, frequency, and/or duration. For example, the voltage can range for 0-14 V, 2-7 V, and/or 2-4.8 V, the current can range from 0-700 mA, 0-25.4 mA, 0-20 mA, and/or up to 12 mA, the frequency can range from 0.5-1200 Hz, 7-200 Hz, 40-240 Hz, 1-150 Hz, 0-120 Hz, 4-80 Hz, and/or up to 1000 Hz, and the duration can range from 100 µs to 100 ms, 10-2000 µs, 40-1000 µs, 50-400 µs, 50-300 µs, 140-400 µs, 2-200 µs, and/or 740-790 ms. In one embodiment, the stimulation required for a nerve block, i.e., hyperpolarizing the nerves and/or nerve fibers of the thoracic region to reduce and/or block the pain signal(s) from propagating, will likely need to be a high frequency alternating current (HFAC) type. Thus, a high frequency of 10 kHz to 20 kHz may be preferred. However, a frequency range of, for example, 5 kHz to 40 kHz, could achieve adequate electrical stimulation.

In one embodiment, the electrical signals and/or electrical stimulation is programmed to be continuous, such that the repolarization of the nerves and/or nerve fibers of the thoracic region is prevented, while the hyperpolarization of the nerves and/or nerve fibers and the reduction and/or prevention of the propagation of the pain signals is continued. However, the electrical signals and/or electrical stimulation can be programmed to be continuous, pulsed, and/or a combination of both. The controller of the pulse generator can save and/or modify a plurality of programmed electrical signals and/or electrical stimulation based on the various parameters of, for example, voltage, current, frequency, and/or duration. Accordingly, a medical professional such as, for example, physician, nurse, medical technician, and/or the patient can adjust the electrical stimulation (e.g., the level of the electrical stimulation) by altering the various parameters discussed above to achieve optimal pain relief. Moreover, the electrical stimulation can be adjusted and the adjusted or set parameters for the electrical stimulation can be saved using, for example, the controller, such that an individual setting can be saved to offer the patient personalized therapy to optimally reduce pain. In one embodiment, the pulse generator and/or the controller include a user interface and one or more microprocessors. The user interface (e.g., a small LCD display) allows for the user, e.g., medical professional, such as the physician, nurse, medical technician, and/or patient, to select, to adjust, and/or to save certain electrical stimulation programs and/or parameters (e.g., voltage, current, frequency, duration, and/or waveform properties) of the electrical signals or electrical stimulation. Moreover, the pulse (or waveform) generator and/or the user interface can be controlled by the one or more microprocessors. The pulse (or waveform) generator and/or the controller are preferably battery operated. While the pulse (or waveform) generator and/or the controller may be configured to be plugged into a power source, a battery, including a rechargeable battery, is preferred. In one embodiment, the power source can be provided via a suction device provided with the chest tube device. The controller may also include a remote control. As discussed above, the chest tube device functions as a chest tube by draining air and/or fluid (e.g., pleural effusion and/or blood) from the thoracic region, while also electrically stimulating the peripheral nerves and/or nerve fibers of the thoracic region. Accordingly, the chest tube device preferably includes a plurality of drainage holes to drain blood, pleural effusion and/or air from the pleural space or cavity surrounding at least one of the lungs. In one embodiment, the chest tube device is about 12-30 inches long or, more preferably, about 20-24 inches long, with a diameter of about 16-46 Fr or, more preferably, about 24-28 Fr. The size and/or diameter of the chest tube device preferably obeys Fanning's Equation ($v=2r\ 5P/fl$, where v is flow, r is the radius, l is the length, P is pressure, and f is the friction factor) to ensure effective drainage of effluent. Using Fanning's Equation, in one embodiment, the chest tube device has a length of 2-11 mm and a diameter of 6-40 Fr. Thus, the chest tube device should not affect flow rates and/or cause blockage or occlusion of the fluid (e.g. blood and/or pleural effusion). The chest tube device is preferably flexible, yet stiff enough to resist kinking during insertion and collapse after insertion. In one embodiment, the chest tube device is prepared from polymers that include, for example, thermoplastic polyurethane, silicone, and/or PVC or any other biomedical grade polymer suitable for thoracic applications, with tensile strengths in the range of, for example, 20-80 MPa3. In one embodiment, the chest tube device is biocompatible and non-cancerogenic. Since the chest tube device is generally placed within a wound due to a surgical procedure and/or a medical condition affecting the thoracic region, the chest tube device is preferably non-thrombogenic (e.g., the outer surface of the chest tube device should not interfere with the wound healing process and clot formation at the site of injury, but should prevent clotting within the chest tube itself). Wound repair can also be enhanced by including, for example, controlled-released drugs, antibiotics, anti-bacterial agents, growth factors and/or bioactive agents with the chest tube device. Moreover, with respect to wound repair outside of the chest tube device and/or clot formation within the chest tube device, the chest tube device is preferably made with a polymer that will neither inhibit nor promote clot formation on the internal or external surface. For example, polyurethane and/or silicone are biomedical polymers, which are generally used in a range of blood contacting applications (e.g., catheters, pacemakers, etc.), that could be used as the polymers for the chest tube device. In addition, clot formation inside the chest tube device could also be addressed by introducing, for example, an inner lining within the chest tube device that contains an anti-clotting agent. The chest tube device should also be sterile. In one embodiment, the chest tube device is resistant to the attachment of bacteria by, for example, adding an anti-bacterial agent (e.g., silver nitrate) to the exterior and/or interior surface of the device. In another embodiment, the chest tube device has a low coefficient of friction to allow for ease of insertion into the thoracic region of the patient. Moreover, the chest tube device should be easy to remove without causing extra patient discomfort. In one embodiment, the chest tube device has a radioopaque strip so that the placement of the device can be monitored, if necessary. In yet another embodiment, the proximal end of the chest tube device (i.e., the end of the device that remains outside of the body of the patient once the device is placed within the thoracic region) easily attaches to accessory tubing that is provided to, for example, collect the blood, pleural effusion, and/or air that is being drained and/or to provide additional suction to assist in the drainage of blood, pleural effusion and/or air. In another embodiment, the chest tube device includes key safety features to avoid adverse side effects, such as burns, blisters, lacerations, itching and/or irritation to the adjacent skin and/or tissues. In one embodiment, an intermediate impedance check is included with the chest tube device to ensure the electrodes and/or conductive materials do not cause burns or transmit excessively painful or damaging high current densities to the adjacent tissues. With regard to placement and/or removal of the chest tube device, in one embodiment, the chest tube device is placed within the thoracic region of a patient in an outpatient room. Accordingly, the placement of the chest tube device is less invasive than the conventional placement of intrathecal devices (e.g., SCS devices) that provide neurostimulation to the spinal cord or brain for pain relief and/or pain management. Such intrathecal devices are generally inserted with invasive procedures that take place in an operating room.

Moreover, since the neurostimulation is provided with the chest tube device, the neurostimulation element is removed once the chest tube device is removed from the thoracic region of the patient. Thus, an additional invasive procedure would not be required for removal of the neurostimulation device, as in the case with intrathecal devices. Moreover, the ability to remove the chest tube device once the pain is alleviated is beneficial and unique, as compared with most neurostimulation devices.

By providing a chest tube device that incorporates neurostimulation, both pleural drainage and pain management issues can be addressed within a single procedure. The chest tube device is designed to reduce pain caused by placement of the chest tube within the thoracic region of the patient and breathing with the chest tube in place. With effective pain reduction, patients would be able to take deeper, unlabored breaths, which are proven to reduce the incidence of atelectasis (e.g., collapse of air space in the lung) and pneumonia (e.g., infection of the lung). Moreover, patients' quality of life could increase as fewer drugs would have to be administered to decrease pain, and, subsequently, fewer side effects would be induced that are associated with the drug use. The reduction of narcotics would be significant for the quality of life of various patients, including, for example, patients with issues of addiction or patients with balance issues that can fall under the influence of narcotics, such as patients that are at least 72 years old. In particular, the decreased use of narcotics could prevent respiratory compromise, constipation, and/or risk of injury from falling by improving cognitive ability in eldering patients.

Furthermore, the decreased use of narcotics could prevent opioid dependence and/or addiction, low ventilation as well as hyperalgesic syndrome. The chest tube device is also expected to have an increased therapeutic effect and require less time and resources to be placed when compared to both intrapleural catheters and intrathecal devices. The chest tube device has the potential to improve quality of life and post-operative immune response, while also decreasing recovery time and/or reducing the odds of hyperalgesic and chronic pain syndromes as well as infection of the lung (e.g. pneumonia). By using the chest tube device described above, the patient would likely have improved pulmonary function, as he or she would not be in pain while breathing. By improving pulmonary function, the patient would likely have a lower rate of infection (e.g. pneumonia), faster recovery time with less hospitalization time and lower cost for the overall thoracic procedure. In view of the foregoing, the chest tube device described above provides a novel approach to post-thoracic surgery and/or interventional pain management.

The chest tube device of the present disclosure provides an effective way to drain air and/or fluid (e.g., pleural effusion and/or blood) from the thoracic region of a patient, while also electrically stimulating the peripheral nerves and/or nerve fibers of the thoracic region to reduce and/or prevent the propagation of pain signals that typically result from the placement of a chest tube in the thoracic region of a patient. More specifically, the present disclosure relates to a chest tube device that incorporates neurostimulation to address both pleural drainage and pain management issues within a single procedure.

Various examples of aspects of the disclosure are described below as clauses for convenience. These are provided as examples, and do not limit the subject technology.

Clause A. A chest tube device with neurostimulation, the chest tube device comprising a tubular member, and an electro-analgesic region to provide neurostimulation to at least one of (i) one or more peripheral nerves and (ii) one or more nerve fibers of a thoracic region of a patient.

Clause B. A chest tube device with neurostimulation, the chest tube device comprising a tubular member, an electro-analgesic region to provide neurostimulation to at least one of (i) one or more peripheral nerves and (ii) one or more nerve fibers of a thoracic region of a patient, a suction device to assist in draining at least one of blood, pleural effusion, and air from the thoracic region, and a pulse generator that provides electrical signals to the electro-analgesic region.

Clause C. A method of reducing pain associated with the placement of a chest tube in a thoracic region of a patient, the method comprising inserting a chest tube device into a pleural space of a patient, between the lung and chest wall and at least one of the ribs of the patient, and electrically stimulating at least one of (i) one or more peripheral nerves and (ii) one or more nerve fibers of the thoracic region of the patient.

Clause D. A method of suppressing pain associated with the placement of a chest tube in a thoracic region of a patient, the method comprising inserting a chest tube device into a pleural space of a patient, between the lung and chest wall and at least one of the ribs of the patient, and electrically stimulating at least one of (i) one or more peripheral nerves and (ii) one or more nerve fibers of the thoracic region of the patient.

Clause E. A method of mitigating pain associated with the placement of a chest tube in a thoracic region of a patient by at least one of (i) reducing an amount of pain signals from being transmitted to the brain of the patient and (ii) preventing pain signals from being transmitted to the brain of the patient, the method comprising inserting a chest tube device into a pleural space of a patient, between the lung and chest wall and at least one of the ribs of the patient, and electrically stimulating at least one of (i) one or more peripheral nerves and (ii) one or more nerve fibers of the thoracic region of the patient.

Clause F. A method of electrically stimulating at least one of (i) one or more peripheral nerves and (ii) one or more nerve fibers of a thoracic region of a patient, to reduce pain in patients undergoing chest tube implantation, the method comprising electrically stimulating at least one of (i) one or more peripheral nerves and (ii) one or more nerve fibers of the thoracic region of the patient, and hyperpolarizing the at least one of (i) one or more peripheral nerves and (ii) one or more nerve fibers of the thoracic region to reduce an amount of pain signals from being transmitted to the brain of the patient.

Clause G. A method of electrically stimulating at least one of (i) one or more peripheral nerves and (ii) one or more nerve fibers of a thoracic region of a patient, to suppress pain in patients undergoing chest tube implantation, the method comprising electrically stimulating at least one of (i) one or more peripheral nerves and (ii) one or more nerve fibers of the thoracic region of the patient, and hyperpolarizing the at least one of (i) one or more peripheral nerves and (ii) one or more nerve fibers of the thoracic region to prevent pain signals from being transmitted to the brain of the patient.

Clause H. A method of electrically stimulating at least one of (i) one or more peripheral nerves and (ii) one or more nerve fibers of a thoracic region of a patient to mitigate pain in patients undergoing chest tube implantation, the method comprising electrically stimulating at least one of (i) one or more peripheral nerves and (ii) one or more nerve fibers of the thoracic region of the patient, and hyperpolarizing the at least one of (i) one or more peripheral nerves and (ii) one or more nerve fibers of the thoracic region to at least one of (i) reduce an amount of pain signals from being transmitted to the brain of the patient and (ii) prevent pain signals from being transmitted to the brain of the patient.

In one or more aspects, examples of additional clauses are described below.

Element 1: the tubular member includes a plurality of drainage holes to drain at least one of blood, pleural effusion, and air from the thoracic region.

Element 2: a suction device to assist in draining the at least one of blood, pleural effusion, and air from the thoracic region.

Element 3: a pulse generator that provides electrical signals to the electro-analgesic region.

Element 4: the electro-analgesic region is disposed along a surface of the tubular member of the chest tube device.

Element 5: the electro-analgesic region comprises at least one of (i) a conductive wire mesh, (ii) a stimulation sleeve, (iii) a conductive material, (iv) a conductive polymer, (v) electro-stimulating leads, and (vi) one or more electrodes.

Element 6: the electro-analgesic region comprises a conductive material that includes at least one of (i) strips of conductive material, (ii) a coil of conductive material, (iii) a plurality of particles of conductive material, (iv) a sheath of conductive material, and (v) one or more electrically conductive rings.

Element 7: the electro-analgesic region comprises an electrically conductive polymer.

Element 8: the electro-analgesic region comprises a plurality of electrically conductive rings provided along an exterior surface of the tubular member of the chest tube device.

Element 9: a power source that comprises at least one of an A/C adapter, a battery, and a rechargeable battery.

Element 10: a pulse generator that provides electrical signals to the electro-analgesic region.

Element 11: a controller to adjust at least one of (i) a voltage, (ii) a current, (iii) a frequency, (iv) a duration, and (v) a waveform of the electrical signals.

Element 12: the voltage of the electrical signals is between about 0 V and 14 V.

Element 13: the current of the electrical signals is between about 0 mA and 700 mA.

Element 14: the frequency of the electrical signals is between about 0.5 Hz and 10,000 Hz.

Element 15: the duration of the electrical signals is between about 10 µs to 790 ms.

Element 16: the step of electrically stimulating the at least one of (i) one or more peripheral nerves and (ii) one or more nerve fibers of the thoracic region hyperpolarizes the at least one of (i) one or more peripheral nerves and (ii) one or more nerve fibers of the thoracic region to reduce an amount of pain signals from being transmitted to the brain of the patient.

Element 17: the step of electrically stimulating the at least one of (i) one or more peripheral nerves and (ii) one or more nerve fibers of the thoracic region is provided by an electro-analgesic region that is disposed on a surface of the chest tube device.

Element 18: the electro-analgesic region is disposed adjacent to at least one of (i) one or more peripheral nerves and (ii) one or more nerve fibers of the thoracic region, after the inserting of the chest tube device into the pleural space of the patient.

Element 19: the electro-analgesic region comprises at least one of (i) a conductive wire mesh, (ii) a stimulation sleeve, (iii) a conductive material, (iv) a conductive polymer, (v) electro-stimulating leads, and (vi) one or more electrodes.

Element 20: the chest tube device includes a pulse generator to provide electrical signals to the electro-analgesic region.

Element 21: a step of adjusting at least one of (i) a voltage, (ii) a current, (iii) a frequency, (iv) a duration, and (v) a waveform of the electrical signals.

Element 22: the step of draining at least one of blood, pleural effusion, and air from the thoracic region.

Element 23: the step of applying suction to assist in draining the at least one of blood, pleural effusion, and air from the thoracic region.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A chest tube device with neurostimulation, the chest tube device comprising:
   a tubular member; and
   an electro-analgesic region to provide neurostimulation to (i) one or more peripheral nerves and (ii) one or more nerve fibers of a thoracic region of a patient during recovery from a thoracic procedure,
   wherein the electro-analgesic region comprises a plurality of strips of conductive material extending horizontally along a length of the tubular member,
   wherein the electro-analgesic region has a length that is substantially a same length as the thoracic region and wherein the electro-analgesic region provides the neurostimulation to reduce pain associated with the placement of the chest tube device in the thoracic region of the patient.

2. The chest tube device of claim 1, wherein the tubular member includes a plurality of drainage holes along an exterior surface of the tubular member to drain at least one of blood, pleural effusion, and air from the thoracic region.

3. The chest tube device of claim 2, further comprising a suction device to assist in draining the at least one of blood, pleural effusion, and air from the thoracic region.

4. The chest tube device of claim 3, further comprising a pulse generator that automatically provides electrical signals to the electro-analgesic region without user intervention during recovery.

5. The chest tube device of claim 1, wherein the electro-analgesic region is disposed along an entire distal surface of the tubular member of the chest tube device.

6. The chest tube device of claim 5, where the electro-analgesic region further comprises at least one of (i) a conductive wire mesh, (ii) a stimulation sleeve, (iii) a conductive polymer, (iv) electro-stimulating leads, and (v) one or more electrodes.

7. The chest tube device of claim 6, wherein the electro-analgesic region comprises an electrically conductive polymer.

8. The chest tube device of claim 6, wherein the electro-analgesic region comprises a plurality of electrically conductive rings provided along an exterior surface of the tubular member of the chest tube device.

9. The chest tube device of claim 1, further comprising a power source that comprises at least one of an A/C adapter, a battery, and a rechargeable battery.

10. The chest tube device of claim 1, further comprising a pulse generator that provides electrical signals to the electro-analgesic region.

11. The chest tube device of claim 10, further comprising a controller to adjust at least one of (i) a voltage, (ii) a current, (iii) a frequency, (iv) a duration, and (v) a waveform of the electrical signals.

12. The chest tube device of claim 11, wherein the voltage of the electrical signals is between about 0 V and 14 V.

13. The chest tube device of claim 11, wherein the current of the electrical signals is between about 0 mA and 700 mA.

14. The chest tube device of claim 11, wherein the frequency of the electrical signals is between about 0.5 Hz and 10,000 Hz.

15. The chest tube device of claim 11, wherein the duration of the electrical signals is between about 10 μs to 790 ms.

16. The chest tube device of claim 1, wherein the electro-analgesic region is not activated during the thoracic procedure.

17. A chest tube device with neurostimulation, the chest tube device comprising:
    a tubular member;
    an electro-analgesic region to provide neurostimulation to (i) one or more peripheral nerves and (ii) one or more nerve fibers of a thoracic region of a patient during recovery from a thoracic procedure;
    a suction device to assist in draining at least one of blood, pleural effusion, and air from the thoracic region; and
    a pulse generator that automatically provides electrical signals to the electro-analgesic region after in situ placement of the chest tube device,
    wherein the an electro-analgesic region comprises a coil of conductive material helically wound around the tubular member,
    wherein the electro-analgesic leg on has length that is substantially a same length as the thoracic region and wherein the electro-analgesic region provides the neurostimulation to reduce pain associated with the placement of the chest tube device in the thoracic region of the patient.

18. A method of reducing pain associated with the placement of a chest tube in a thoracic region of a patient, the method comprising:
    inserting a chest tube device into a pleural space of a patient, between the lung and chest wall and at least one of the ribs of the patient; and
    electrically stimulating (i) one or more peripheral nerves and (ii) one or more nerve fibers of the thoracic region of the patient during recovery from a thoracic procedure, wherein the chest tube device comprises a coating of an electrically conductive polymer near a distal end of the chest tube device for providing the stimulation, and
wherein the coating extends a length of the chest tube that is substantially a same length as the thoracic region.

19. The method of claim 18, further comprising a step of adjusting at least one of (i) a voltage, (ii) a current, (iii) a frequency, (iv) a duration, and (v) a waveform of the electrical signals.

20. The method of claim 18, further comprising the step of draining at least one of blood, pleural effusion, and air from the thoracic region.

\* \* \* \* \*